US005204481A

United States Patent [19]

[11] Patent Number: 5,204,481

Carroll et al.

[45] Date of Patent: Apr. 20, 1993

[54] PROCESS FOR PREPARING BENZOTHIAZOLE SULFENIMIDES USING AN ALIPHATIC HYDROCARBON SOLVENT

[75] Inventors: Sharen B. Carroll, Akron; Horng-Jau Lin, Wadsworth; Roger K. Rains, Richfield, all of Ohio

[73] Assignee: Monsanto Company, St. Louis, Mo.

[21] Appl. No.: 894,965

[22] Filed: Jun. 8, 1992

[51] Int. Cl.[5] .................. C07C 277/62; C07C 277/68; C07C 277/76

[52] U.S. Cl. .................................... 548/157; 548/166; 548/167

[58] Field of Search ........................ 548/157, 166, 167

[56] References Cited

U.S. PATENT DOCUMENTS 3,151,122 9/1964 Sundholm ....................... 548/157 X
3,705,923 12/1972 Sullivan .............................. 548/166

OTHER PUBLICATIONS

Chemical; Abstracts 87:152063, Ignatov, V. A. et al. (USSR) (1978).

*Primary Examiner*—Floyd D. Higel
*Attorney, Agent, or Firm*—Gordon B. Seward

[57] ABSTRACT

An improved process for producing N-alkyl or N-cycloalkyl-2-benzothiazole sulfenimides uses aliphatic hydrocarbons as a reaction medium in converting N-alkyl or N-cycloalkyl-2-benzothiazole sulfenamides to the corresponding sulfenimides by reaction with an acid.

9 Claims, No Drawings

PROCESS FOR PREPARING BENZOTHIAZOLE SULFENIMIDES USING AN ALIPHATIC HYDROCARBON SOLVENT

FIELD OF THE INVENTION

This invention relates to an improved process for producing N-alkyl- and N-cycloalkyl-2-benzothiazole sulfenimides.

BACKGROUND

U. S. Pat. No. 3,151,122 to Sundholm discloses a process for producing N-alkyl- and N-cycloalkyl-2-benzothiazole sulfenimides(described in the patent as N-alkyl- and N-cycloalkylbis (2-benzothiazolesulfen)amides). The process of the patent reacts N-alkyl- or N-cycloalkylbenzothiazole sulfenamides with one half an equivalent of an acid having an ionization constant, $K_a$, above 0.001, in a solvent for the starting 2-benzothiazole sulfenamide compound. Recommended solvents include benzene, toluene, solvent naphtha, chlorobenzene, carbon tetrachloride, methylene chloride, ethylene chloride, propylene chloride, mixed amyl chlorides, ethyl ether and dioxane and mixtures thereof (col. 3, lines 6–13).

BRIEF SUMMARY OF THE INVENTION

The invention is directed to the process for producing N-alkyl- or N-cycloalkyl-2-benzothiazole sulfenimides by the reaction, in aliphatic hydrocarbons, of the corresponding N-alkyl or N-cyclo-alkyl-2-benzothiazole sulfenamides with an acid having an ionization constant, $K_a$, which is greater than 0.001 at 25° C.

In contrast to the prior art, the process of the invention performs the reaction in a reaction medium which consists essentially of aliphatic hydrocarbons, selected for their property of having very limited solubilities for the starting material and for the product. Several advantages flow from the use of the reaction media of the invention. First, almost all of the product is in the form of a slurry in the reaction medium, thus greatly enhancing the recovery process, which can be simple filtration, with evaporation of entrained hydrocarbon. Second, the media of the invention are among those materials which are not restricted by governmental regulations, as "SARA-listed" substances. Surprisingly, the process of the invention gives yields which are superior to those achieved with the solvents recommended in the above-cited patent, despite the fact that neither the starting sulfenamide material nor the sulfenimide product is more than slightly soluble in the reaction media.

DETAILED DESCRIPTION

The sulfenamide starting materials are well-known compounds, which can be prepared by the oxidative reaction of 2-mercaptobenzothiazole with an alkyl or cycloalkyl primary amine, such as isopropylamine, t-butylamine or cyclohexylamine. The sulfenamides thus produced, N-isopropyl-2-benzothiazole sulfenamide, N-t-butyl-2-benzothiazole sulfenamide and N-cyclohexyl-2-benzothiazole sulfenamide, are widely used as accelerators in the sulfur vulcanization of rubber. Similarly, other alkyl or cycloalkyl primary amines can be employed to produce the corresponding sulfenamide starting materials. Preferred are the sulfenamides from isopropylamine, t-butylamine and cyclohexylamine.

The acid reactants of the invention can be any acids which have ionization constants greater than 0.001. Examples include hydrochloric acid, hydrobromic acid, sulfuric acid, chloroacetic acid, bromoacetic acid, o-chlorobenzoic acid, o-nitrobenzoic acid and the like. Of these acids, hydrochloric acid is preferred.

The preferred temperature of the process of the invention is between 15° C. and 40° C.

The reaction is preferably performed under essentially anhydrous conditions, as experiments have shown that the presence of even a small amount of water (0.05 weight percent) in the reaction medium will adversely affect both the yield and the purity of the product. Since water can also enter the reactor with the reactants, efforts should be made to minimize their water content, as well.

The reaction media of the invention are aliphatic hydrocarbons. Included are straight-chain, branched-chain and cyclic aliphatic hydrocarbons containing 5–8 carbon atoms, and mixtures thereof. Preferred are heptanes.

The products of the process of the invention, N-alkyl- or N-cycloalkyl-2-benzothiazole sulfenimides, are also accelerators for the sulfur-vulcanization of rubber, characterized by long scorch delay and relatively slow cure rates. The preferred products, N-isopropyl-, N-t-butyl- and N-cyclohexyl-2-benzothiazole sulfenimide have been shown to be especially effective in vulcanizing rubber articles having relatively thick cross-sections. In these applications, the relatively slow cure rate achieved gives evenly-cured vulcanizates which are neither undercured at the center nor overcured at the edges.

A better understanding of the invention can be obtained by reference to the following illustrative examples, in which all percentages are by weight and all temperatures are in degrees centigrade unless otherwise indicated.

EXAMPLE 1

Addition of HCl to a slurry of TBBS in heptane

Into a 1000 ml resin flask equipped with an agitator, condenser, subsurface gas feed tube, and thermometer was charged 500 ml of dry heptane and 59.6 g (0.25 m) of TBBS (N-t-butyl-2-benzothiazole sulfenamide) at 25° C.–30° C. With the agitator on, 4.6 g (0.125 m) of anhydrous HCl was added over a period of one hour. The reaction temperature was allowed to rise to 35° during the HCl feed. The mixture was then cooled to 24° C.–26° C. over a one half hour period. The reaction solids consisting of product plus t-butylamine hydrochloride were separated from heptane by vacuum filtration, washing with 100 ml heptane and drying. The dry mixed solids were slurried in water to dissolve the hydrochloride salt, then the product was isolated by vacuum filtration, water washing and drying. Dry product, N-t-butyl-2-benzothiazole sulfenimide, with an HPLC assay of 95.5 area %, was obtained in 91.4% yield (46.1 g) from TBBS.

EXAMPLE 2

Concurrent addition of HCl and TBBS

Into a 1000 ml resin flask equipped with an agitator, condenser, subsurface gas feed tube, solids addition funnel and thermometer was charged 600 ml of dry liquid aliphatic hydrocarbon (Ashland A-140). With the agitator on, about 6 g or 8.4% of the total charge of TBBS (N-t-butyl-2-benzothiazole sulfenamide) was added to the vessel. Then 5.4 g (0.15 m) of anhydrous HCl and the rest of the 71.4 g (0.3m) total TBBS charge were concurrently added over a one hour period, such that HCl feed finished two minutes after completion of TBBS feed. Reaction temperature was 22° C.-25° C. The reaction solids (product plus t-butylamine hydrochloride) were separated from the solvent by vacuum filtration and solvent washing. The mixed solids were slurried in water to dissolve the hydrochloride salt and then product was isolated by vacuum filtration, water washing and drying. Dry product, N-t-butyl-2-benzothiazole sulfenimide, with an HPLC assay of 93.7 area %, was obtained in 95.7% yield (57.8 g) from TBBS.

Solubility measurements of the product N-t-butyl-2-benzothiazole sulfenimide in toluene were compared with those for heptanes. The results showed that an average of about 25 times as much of the product was soluble in toluene as in heptane in the temperature range of 15° C.-40° C. This difference is reflected in the amount of product lost in the solvent during the filtration and washing steps. The savings in recovered product, coupled with the relative ease of product recovery when it is in slurry form, produces a clear superiority of the aliphatic hydrocarbons over previously known solvents as reaction media.

What is claimed is:

1. In the process of producing N-alkyl- or N-cycloalkyl-2-benzothiazole sulfenimides by the reaction of the corresponding N-alkyl- or N-cycloalkyl-2-benzothiazole sulfenamide with an acid having an ionization constant, $K_a$, which is greater than 0.001 at 25° C., the improvement wherein the reaction is performed in a reaction medium consisting essentially of aliphatic hydrocarbons, in which reaction medium neither the starting sulfenamide material nor the sulfenimide product is more than slightly soluble.

2. The process of claim 1 wherein the reaction medium is selected from $C_{5-8}$ alkanes and mixtures thereof.

3. The process of claim 1 performed at 15 to 40° C.

4. The process of claim 3 wherein the acid is hydrochloric acid.

5. The process of claim 2 wherein the reaction medium is heptanes.

6. The process of claim 1 performed under essentially anhydrous conditions.

7. The process of claim 4 wherein the sulfenamide is N-t-butyl-2-benzothiazole sulfenamide.

8. The process of claim 4 wherein the sulfenamide is N-cyclohexyl-2-benzothiazole sulfenamide.

9. The process of claim 6 wherein the reaction medium contains less than 0.05 weight percent of water.

* * * * *